United States Patent [19]

Johnson et al.

[11] Patent Number: 4,882,106
[45] Date of Patent: Nov. 21, 1989

[54] METHODS OF MANUFACTURING NUCLEOPHILIC MATERIAL MODIFIED FOR IMPROVED BIOCOMPATIBILITY

[75] Inventors: Richard J. Johnson, Mundelein; Dennis E. Chenoweth, Kildeer; Daniel R. Boggs, Vernon Hills; Michael J. Lysaght, Barrington, all of Ill.

[73] Assignee: Baxter Travenol Laboratories, Inc., Deerfield, Ill.

[21] Appl. No.: 24,652

[22] Filed: Mar. 11, 1987

Related U.S. Application Data

[63] Continuation-in-part of Ser. No. 20,794, Feb. 27, 1987.

[51] Int. Cl.$^4$ .............................................. B01D 13/00
[52] U.S. Cl. .................................. 264/41; 210/500.24; 210/500.29; 264/178 F; 264/199
[58] Field of Search .............. 210/638, 500.24, 500.29, 210/632; 264/41, 178 F, 199

[56] References Cited

U.S. PATENT DOCUMENTS

| | | | |
|---|---|---|---|
| 3,816,402 | 6/1974 | Wilkinson | 260/225 |
| 4,276,172 | 6/1981 | Henne et al. | 210/500.24 X |
| 4,284,594 | 8/1981 | Joh et al. | 210/500.23 X |
| 4,329,383 | 5/1982 | Joh | 210/500.24 X |
| 4,361,484 | 11/1982 | Larsson et al. | 210/632 |
| 4,637,880 | 1/1987 | Halbert | 210/638 |

FOREIGN PATENT DOCUMENTS 3341113 5/1985 Fed. Rep. of Germany ...................... 210/500.24

OTHER PUBLICATIONS

Mauzac et al., "Anticomplementary Activity of Dextran Derivatives", from Biomaterials, 1/1985, pp. 61–63.

Primary Examiner—Frank Spear
Attorney, Agent, or Firm—Charles R. Mattenson; Paul C. Flattery

[57] ABSTRACT

A material is formed into hollow fiber form, and the surface characteristics of the interior bore is selectively modified in a predetermined fashion by a reactive lumen fluid. Nucleophilic materials, such as regenerated cellulose, can be formed into hollow fibers and simultaneously modified to improve their biocompatibility in accordance with the invention.

12 Claims, 8 Drawing Sheets

WHERE X IS:

−CH₂−N(CH₂CH₃)₂ (DIALKYLAMINOALKYL)

−CH₂CH₂−SO₃⁻ (SULFOPROPYL)

(CARBOXYLMETHYL)

−PO₄ (PHOSPHOCELLULOSE)

EUROPEAN APPLICATION 0 172 437

CELLULOSE ACETATE

FILL

DRAIN

WASH

METHODS OF MANUFACTURING NUCLEOPHILIC MATERIAL MODIFIED FOR IMPROVED BIOCOMPATIBILITY

RELATED APPLICATION

This is a continuation-in-part of Chenoweth et al. U.S. patent application Ser. No. 020,794, filed Feb. 27, 1987 and entitled "Nucleophilic Material Modified for Improved Biocompatibility".

FIELD OF INVENTION

In one aspect, the invention relates to improved biocompatible materials suited for contact with biological systems.

In another aspect, the invention relates to membranes intended for use in hemodialysis, and to the modification of these membranes to improve their biocompatibility. More particularly, this aspect of the invention relates to reducing the incidence of or extent to which hemodialysis membranes activate the human complement system.

BACKGROUND OF THE INVENTION

Materials which, in use, come into contact with whole blood, plasma, or other biological systems should not artificially disrupt the biological status quo of the system. This desirable characteristic is sometimes generally referred to as the "biocompatibility" of the material.

It has been observed that certain hemodialysis membranes can, when in contact with blood, activate the human complement system. It is believed that this contributes to a phenomenon called hemodialysis leukopenia, which is a temporary sequestration of leukocytes in the pulmonary vascular system of a small number of patients undergoing hemodialysis.

Cellulosic membranes manufactured by the cuprammonium process (also referred to as regenerated cellulose) have been associated with higher incidences of complement activation than other membrane materials, such as polyacrylonitrile, polycarbonate, and cellulose acetate. See, for example, Chenoweth et al, "Anaphylatoxin Formation During Hemodialysis: Effects of Different Dialyzer Membranes", *Kidney International*, Vol. 24 (1983), pp. 770–774; Chenoweth, "Biocompatibility of Hemodialysis Membranes", *ASAIO*, April–June 1984, Vol 7, No. 2, pp. 44–49; Chenoweth, "Complement Activation During Hemodialysis: Clinical Observations. Proposed Mechanisms, and Theoretical Implications," Artificial organs, 8(3), 1984, pp. 281–287; and Chenoweth et al., Compartmental Distribution of Complement Activation Products in Artificial Kidneys," *Kidney International* Vol 30, pp. 74–80 (1986).

As is shown in FIG. 1A, the surface of regenerated cellulosic membranes includes appended hydroxyl groups (designated OH) and perhaps, as impurities, appended amino groups (designated $NH_2$). These groups are nucleophilic in nature, meaning that they have the natural tendency to seek out atoms with a lowered electron density, such as reactive acyl carbon atoms.

By their chemical nature, it is believed that the nucleophilic groups vary in the degree to which they seek out acyl carbon atoms. The amino groups are believed to be more reactive than the hydroxyl groups.

The human complement system includes certain plasma proteins, which are identified in FIG. 1A as Protein C3; Protein C5; and Protein Factors H&I. These proteins are normally inactive. However, with appropriate stimulus, the Proteins C3 and C5 participate in an enzymatic cascade known as complement activation. The Protein Factors H&I serve as inhibitors to control or regulate the complement activation process.

As shown in FIG. 1B, it is believed that, when the plasma proteins come into contact with the nucleophilic surface, such as a regenerated cellulose membrane, a portion of the Protein C3 having activated carbonyl groups (identified as Component C3b) covalently binds to the surface nucleophiles. Another portion of the Protein C3 (identified as Component C3a) is split off and diffuses into the plasma. As this is occurring, a portion of the Protein C5 (identified as component C5b) also adheres to the membrane surface, freeing component C5a into the plasma. These cleavage components C3a and C5a are called anaphylatoxins.

Complement activation on nucleophilic surfaces like the regenerated cellulosics mentioned above occurs because the control Protein Factors H&I do not associate very well with C3b bound to these types of surfaces. Therefore, Factors H&I cannot inhibit the cascade from proceeding.

As shown in FIG. 1C, the freed C5a anaphylatoxin activates granulocytes, causing them to aggregate or become hyperadherent to the pulmonary vasculature. It is believed that this sequestration of the C5a-activated granulocytes manifests itself as leukopenia during dialysis.

The C3a anaphylatoxin does not appear to interact with the biological constituents of the blood. However, its presence can be measured in the blood, and C3a serves as a marker for accurately quantifying the degree of complement activation taking place.

It is believed that the incidence of complement activation associated with polysulfone, polyacrylonitrile, and polycarbonate hemodialysis membranes is relatively low because these membrane materials do not have appended nucleophilic groups. Certain polyacrylonitrile membranes have also been observed to actually bind the C3a and C5a anaphylatoxins, which are cationic in nature, removing them from circulation to limit patient exposure to these bioactive polypeptides.

In cellulose acetate, the nucleophilic characteristics of the regenerated cellulose are modified by covalently reacting an acetate group with some of the nucleophiles (see FIG. 4B). This reduces the number of bio-reactive nucleophiles available to covalently bind the C3b complement protein.

Efforts continue to develop ways of making regenerated cellulose membranes as biocompatible as polysulfone, polyacrylonitrile, polycarbonate, and cellulose acetate membranes. This is in part due to the efficiencies and low costs now associated with the manufacture of regenerated cellulose membranes, compared to other dialysis membranes.

In published European application No. 0 172 437, it is claimed that the incidence of complement activation in regenerated cellulose membranes can be reduced by bulk blending unmodified regenerated cellulose with regenerated cellulose that has been modified with diethylaminoethyl, sulfopropyl, carboxymethyl, or phosphonate alkyl. As described in this published application, about 4 to 40 parts by weight of the unmodified cellulose is blended with 1 part by weight of the modified cellulose.

As in the case of cellulose acetate, the number of bio-reactive nucleophiles associated with the modified cellulose is reduced, as the substituents become covalently bound to some of the nucleophiles (see FIG. 4A). The bound substituents also carry a negative charge and can bind the cationic C3a and C5a anaphylatoxins, removing them from circulation. However, in the blending process described in this published application, only the nucleophiles associated with the modified cellulose are effected. All of the nucleophiles associated with the unmodified cellulose, which constitutes the major constituent of the blend, retain their natural bio-reactive nature.

In addition to biocompatibility, there are other desirable characteristics for materials intended for use as dialysis membranes. One such characteristic involves the ability of the membrane to remove Beta-2-microglobulin and other poorly dialyzed molecules in the 1000 to 20000 molecular weight range. Because regenerated cellulose material does not have the capacity to reduce Beta-2-microglobulin levels, the accumulation of this material in the tissue of dialysis patients has become a focus of concern in the medical community. See, for example, Gejyo F, Homma N, Suzuki Y, Arakawa M: "Serum levels of a B-2-microglobulin as a new form of amyloid protein in patients undergoing long-term hemodialysis." *N Eng J Med* 314 (1986) 585–6; Zingraff J, Beyne P, Bardin T, Touam M, Uzan M, Man NK, Drueke T: "Dialysis amyloidosis and plasma B-2 microglobulin." *Abstracts EDTA-ERA* 23 (1986) p 162; Vandenbroucke JM: "Relationship between membrane characteristics and dialysis induced changes in B-2-microglobulin levels." *Abstracts EDTA-ERA* 23 (1986) p 156; Hauglustaine D, Waer M, Michielsen P, Goebels J, Vanduputte M: "Hemodialysis membranes, serum B-2 microglobulin, and dialysis amyloidosis (letter)" *Lancet* 24 May 1986 p 1211; Granollaras C, Deschodt G, Branger A, Oules R, Shaldon S, Floege J, Koch KM: "B-2-microglobulin kinetics during hemodialysis and hemofiltration (abstract)" *Blood Purification* 4(4) 1986 p 210; and Vincent C., Revillard JP, Galland M. Traeger J: "Serum B-2-microglobulin in hemodialyzed patients." *Nephron* 21 (1978) 260–268.

One of the principal objectives of this invention is to improve the biocompatibility of materials having nucleophilic groups, such as regenerated cellulose. More particularly, it is a principal objective of this invention to provide a process of efficiently treating a material having nucleophilic groups in a way that blocks the covalent bonding of complement proteins and the associated release of anaphylatoxins.

Another principal objective of this invention is to provide a material which will bind bioactive materials, such as the anaphylatoxins, to limit overall patient exposure to the bioreactive materials.

Another principal objective of this invention is to provide a material capable of removing Beta-2- microglobulin and other like material from a biological fluid.

SUMMARY OF THE INVENTION

The invention achieves these and other objectives by modifying a nucleophilic material in a way that significantly reduces the incidence of complement activation. In accordance with the invention, the nucleophilic material is modified with a second material having activated carbonyl groups, employing a specific nucleophilic-acyl substitution reaction which creates a non-ether linkage with the nucleophile, while at the same time retaining a free carboxyl (acid) group.

In accordance with the invention, the modified nucleophilic groups lose their capacity to covalently bind the C3b protein component. The associated release of the C3a and C5a anaphylatoxins is thus blocked.

Also in accordance with the invention, the retention of the free carboxyl group on the modified nucleophilic groups imparts a negative charge to the treated material. It is believed that this favors the binding of the inhibitory Protein Factors H&I to moderate the complement activation process, if started. The negative charge also serves to bind the cationic C3a and C5a anaphylatoxins, removing them from circulation.

As used in this specification, the term "nucleophilic" refers to a hydroxyl group, an amino group, or the like having the general structure:

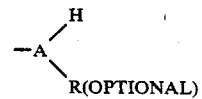

where A is an atom other than carbon; for example, nitrogen, oxygen, or sulphur;

where H is a hydrogen atom; and where R can optionally be another hydrogen atom.

In a preferred embodiment, the second material, which reacts with the nucleophilic groups, is a di-carboxylic acid anhydride, having the general structure:

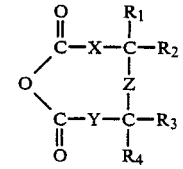

where C is a carbon atom;

where O is an oxygen atom;

where C═O represents the activated carbonyl group;

where X is a sigma bond (i.e., no atom) or an alkane or alkyl derivative or an alkene or alkene derivative or an aryl compound;

where Y is a sigma bond (i.e., no atom) or an alkane or alkyl derivative or alkene or alkene derivative or an aryl compound;

where Z is a sigma bond, a pi bond or an alkane or alkyl derivative or alkene or alkene derivative or an aryl compound;

where $R_1$ is a hydrogen atom; or an alkene or alkyl derivative; alkene or alkene derivative; or aryl compound; or a halide; or any of the following groups: COOH, $SO_3^-$, $SO_4^-$, $PO_4^-$, or DEAE (diethylaminoethyl) moiety; or any primary, secondary or tertiary amine, or any alkyl ether, or thio alkyl ether of the form —OR or —SR, where R is any alkyl, alkenyl or aryl chain, and S is a sulphur atom;

where $R_2$ is a hydrogen atom; or an alkane or alkyl derivative; alkene or alkene derivative; or aryl compound; or a halide; or any of the following groups: COOH, $SO_3^-$, $SO_4^-$, $PO_4^-$, or DEAE (diethylaminoethyl) moiety; or any primary, secondary or tertiary amine, or any alkyl ether, or thio alkyl ether of the form —OR or —SR, where R is any alkyl, alkenyl or aryl chain, and S is a sulphur atom;

where $R_3$ is a hydrogen atom; or an alkane or alkyl derivative; alkene or alkene derivative; or aryl compound; or a halide; or any of the following groups: COOH, $SO_3^-$, $SO_4^-$, $PO_4^-$, or DEAE (diethylaminoethyl) moiety; or any primary, secondary or tertiary amine, or any alkyl ether, or thio alkyl ether of the form —OR or —SR, where R is any alkyl, alkenyl or aryl chain, and S is a sulphur atom; and where $R_4$ is a hydrogen atom; or an alkane or alkyl derivative; alkene or alkene derivative; or aryl compound; or a halide; or any of the following groups: COOH, $SO_3^-$, $SO_4^-$, $PO_4^-$, or DEAE (diethylaminoethyl) moiety; or any primary, secondary or tertiary amine, or any alkyl ether, or thio alkyl ether of the form —OR or —SR, where R is any alkyl, alkenyl or aryl chain, and S is a sulphur atom.

Di-carboxylic acid anhydrides having this general structure include maleic anhydride; succinic anhydride; phthalic anhydride; glutaric anhydride; aconitic anhydride; 2, 3-dimethyl maleic anhydride; 2, 3-dichloromaleic anhydride; and 2, 3, 5, 6-benzene tetracarboxylic acid anhydride.

In another embodiment, the second material is an acid halide having the general structure:

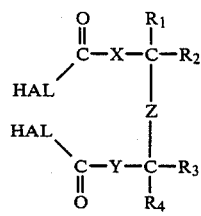

where C is a carbon atom;
where O is an oxygen atom;
where HAL is a halide group such as fluorine chlorine, bromine, or iodide;
where X is a sigma bond (i.e., no atom) or an alkane or alkyl derivative or an alkene or alkene derivative or an aryl compound;
where Y is a sigma bond (i.e., no atom) or an alkane or alkyl derivative or alkene or alkene derivative or an aryl compound;
where Z is a sigma bond, a pi bond or an alkane or alkyl derivative or alkene or alkene derivative or an aryl compound;
where $R_1$ is a hydrogen atom; or an alkane or alkyl derivative; alkene or alkene derivative; or aryl compound; or a halide; or any of the following groups: COOH, $SO_3^-$, $SO_4^-$, $PO_4^-$, or DEAE (diethylaminoethyl) moiety; or any primary, secondary or tertiary amine, or any alkyl ether, or thio alkyl ether of the form —OR or —SR, where R is any alkyl, alkenyl or aryl chain, and S is a sulphur atom;
where $R_2$ is a hydrogen atom; or an alkane or alkyl derivative; alkene or alkene derivative; or aryl compound; or a halide; or any of the following groups: COOH, $SO_3^-$, $SO_4^-$, $PO_4^-$, or DEAE (diethylaminoethyl) moiety; or any primary, secondary or tertiary amine, or any alkyl ether, or thio alkyl ether of the form —OR or —SR, where R is any alkyl, alkenyl or aryl chain, and S is a sulphur atom;
where $R_3$ is a hydrogen atom; or an alkane or alkyl derivative; alkene or alkene derivative; or aryl compound; or a halide; or any of the following groups: COOH, $SO_3^-$, $SO_4^-$, $PO_4^-$, or DEAE (diethylaminoethyl) moiety; or any primary, secondary or tertiary amine, or any alkyl ether, or thio alkyl ether of the form —OR or —SR, where R is any alkyl, alkenyl or aryl chain, and S is a sulphur atom; and where $R_4$ is a hydrogen atom; or an alkane or alkyl derivative; alkene or alkene derivative; or aryl compound; or a halide; or any of the following groups: COOH, $SO_3^-$, $SO_4^-$, $PO_4^-$, or DEAE (diethylaminoethyl) moiety; or any primary, secondary or tertiary amine, or any alkyl ether, or thio alkyl ether of the form —OR or —SR, where R is any alkyl, alkenyl or aryl chain, and S is a sulphur atom.

Acid halides having this general structure include succinyl dichloride and glutaryl dichloride.

In modifying the nucleophilic groups in accordance with the invention, the di-carboxylic acid anhydride or acid halide is reacted with the nucleophilic material for a predetermined time interval. When a di-carboxylic acid anhydride is used, the reaction preferably occurs in the presence of a catalyst, such as pyridine; triethylamine; N-N-dimethyl amino pyridine; or 4-pyrrolidinopyridine. The reaction is stopped after the desired time interval by removing the reaction agents, using, for example, an aqueous wash.

Having been modified in accordance with the invention, the nucleophilic group has the general structure:

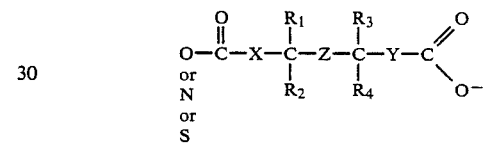

where the non-ether linkage is represented by:

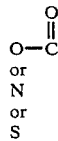

which can take the form of an ester bond:

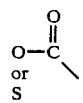

or an amide bond:

and;

where the free carboxyl (acid) group retained by the modified nucleophile is represented by:

The invention is applicable to the treatment of all nucleophilic materials, such as agarose derived material (for example, sepharose or a cross-linked agarose material); amino polystyrene material; or regenerated cellulose material and its derivatives, such as sulfo-propyl cellulose; carboxymethyl cellulose; diethylaminoethyl cellulose; cellulose acetate; phospho cellulose; and the like.

In a preferred embodiment, the material is a regenerated cellulose material suited for use as a hemodialysis membrane and having the general structure:

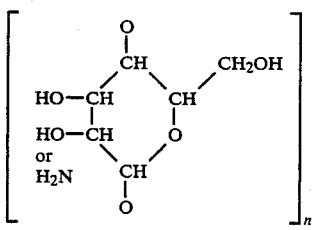

where OH represents a bio-reactive nucleophile consisting of hydroxyl group; and where NH2 represents a bio-reactive nucleophile consisting of an amino group.

In an embodiment where the regenerated cellulose material is treated in accordance with the invention with maleic anhydride, the resulting structure of the modified nucleophilic group is

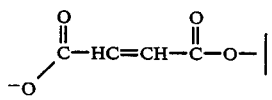

, in the case of a reaction with a hydroxyl group; and

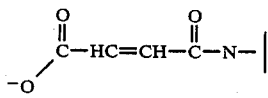

, in the case of a reaction with an amino group.

Because of their chemical nature, the activated carbonyl groups of the di-carboxylic acid anhydride or acid halide will react initially with the most nucleophilic groups. These most nucleophilic groups are also believed to be the most bio-reactive, and as such they will also be the first to bind the similar activated carbonyl groups within the Complement C3b protein.

In this respect, the invention serves to prevent the undesired reaction between nucleophiles and a biological material, by blocking these nucleophiles with a non-biological material. Not only does this modification block the undesired biological reaction, it also imparts additional biologically desirable characteristics.

For example, in addition to modifying the most reactive nucleophiles, the invention generates a surface which displays other advantageous characteristics. In particular, the addition of negatively charged carboxyl groups acts to adsorb biologically active proteins, such as C5a, thus removing them from solution. The increased charge density may also facilitate the interaction of Factors H and I with the surface bound C3b, and thus lead to inactivation of the complement cascade.

It has been observed that the treatment of regenerated cellulose material in accordance with the invention reduces the incidence of complement activation by over 90%, compared to the degree of complement reactivation of untreated regenerated cellulose material. The treatment does not interfere with the material's properties for hemodialysis. After treatment, it remains functionally capable of being used for dialysis.

The invention lends itself to the treatment of bulk polymers, as well as finished medical devices. More particularly, the entire polymer structure of the nucleophilic material may be modified in accordance with the invention during the manufacturing process. However, the invention works more efficiently on a much smaller scale. The nucleophilic groups may be selectively modified in accordance with the invention after the bulk polymer has been made in an unmodified form and incorporated into a medical device, by treating within the medical device only the surface of the material where contact with biological fluids is to actually occur.

Another aspect of the invention involves a method of treating material in hollow fiber form by selectively modifying the surface characteristics of the material only along the interior bore of the hollow fiber. In this aspect of the invention, a reactive constituent is incorporated into a lumen fluid which, when introduced into the fiber bore, modifies the surface characteristics of the bore.

Another aspect of the invention involves the manufacture of material into hollow fiber form while simultaneously altering the surface characteristics of the interior bore of the fiber. In this aspect of the invention, as the material is being formed into a tubular shape, a lumen fluid is introduced into the interior region of the tubular form. The lumen fluid includes a constituent which by reaction with the formed material, modifies or alters the surface characteristics in a predetermined, beneficial fashion along the interior region of the tubular shape.

By introducing the reactive constituent with the lumen fluid, the modification of hollow fiber materials can be selectively controlled and localized to the confines of the interior bore.

In a preferred embodiment, nucleophilic material, such as cellulose, is extruded into hollow fiber form using a lumen fluid having a first constituent, which is immiscible with the nucleophilic material to form the interior bore, and a second constituent, which covalently reacts with nucleophilic groups associated with the material located along the periphery of the interior bore. By locally modifying the nucleophilic groups within the interior bore of the fiber, the incidence of complement activation occasioned by the passage of blood through the interior bore is significantly reduced.

In the embodiment where the nucleophilic material is regenerated cellulose, the first constituent of the lumen fluid is an inactive organic liquid, such as isopropyl myristate. The second constituent of the lumen fluid is preferably selected from the group consisting of di-carboxylic acid anhydrides and acid halides. In this arrangement, the reactive lumen fluid can be washed from the interior bores of the hollow fibers in the process of incorporating the hollow fibers into a finished dialyzer.

DESCRIPTION OF THE SPECIFIC EMBODIMENTS

Figure 2:
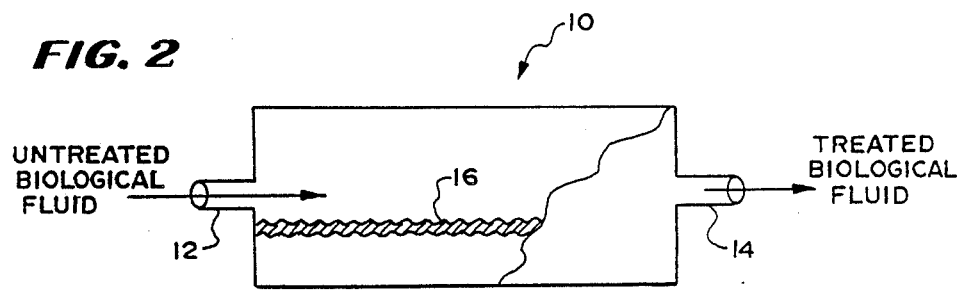
FIG. 2 is a medical device having a material which has been treated in accordance with the invention.

A device 10 for treating a biological fluid is shown in FIG. 2. The device 10 includes an inlet 12, through which untreated biological fluid enters the device. The device 10 also includes an outlet 14, through which the biological fluid exits the device after treatment.

Housed within the device 10 is a material 16 which functions to treat the biological fluid as it passes through the device. In accordance with the invention, the material 16 has been modified to improve its biocompatibility.

The invention is applicable for use in a diverse number of environments where contact between polymer materials and biological fluids occur. For example, the material 16 can constitute a filtration membrane which separates the biological fluid into constituent parts. Alternately, it can constitute an adsorptive material which adsorbs constituent parts of the fluid.

In the illustrated embodiment, the device 10 houses a dialysis membrane 16 made from a regenerated cellulose material, and as cuprammonium rayon. Such a material is manufactured by Membrana AG (formerly Enka AG) and sold under the trade name "Cuprophan".

The membrane 16 is shown in flat sheet form for the purpose of illustration. Usually, the membrane 16 is in the form of hollow fibers. A representative hollow fiber dialysis device and its manufacture are shown in U.S. Pat. No. 4,497,104 which is incorporated into this specification by reference.

In accordance with the invention, the regenerated cellulose material has been modified to reduce the incidence of complement activation occasioned by its contact with human blood during dialysis.

Figure 3A:
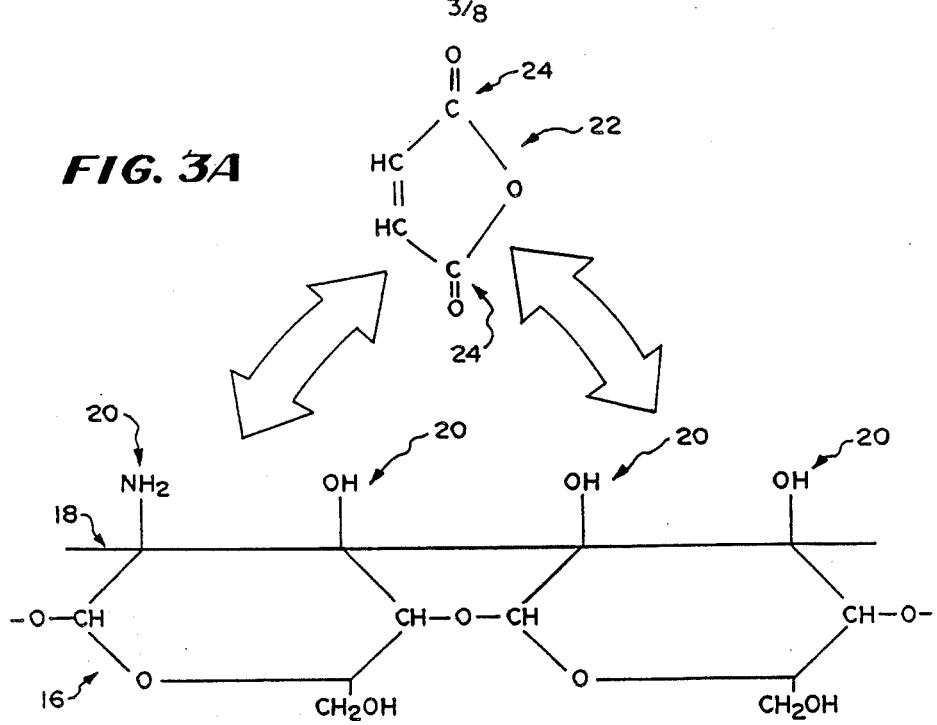
FIGS. 3A and 3B are diagrammatic depictions of regenerated cellulose material undergoing modification in accordance with the invention and the effect of such modification upon the activation of the human complement system.

The surface 18 of the cellulose membrane 16 prior to modification is shown diagrammatically in FIG. 3A. Before modification, the cellulose material 16 includes appended nucleophilic groups 20, or nucleophiles, which are positioned along the surface 18 where contact with human blood will occur. Each nucleophilic group 20 comprises an atom other than carbon (e.g., nitrogen, oxygen, or sulphur) to which at least one hydrogen atom is bonded.

In the particular illustrated embodiment, the nucleophilic groups 20 comprise hydroxyl groups (OH) and amino groups ($NH_2$).

Figure 1A:
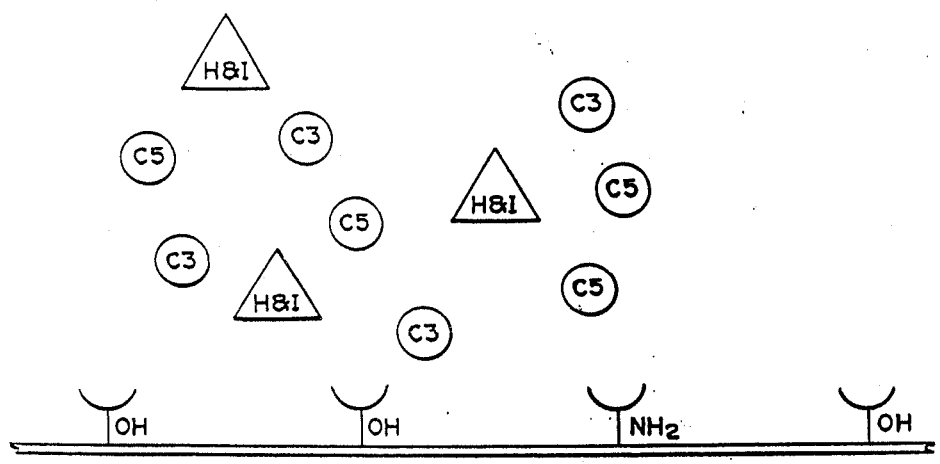
FIGS. 1A and 1C are diagrammatic depictions of the activation of the human complement system in the presence of regenerated cellulose materials before modification in accordance with the invention.
Figure 1B:
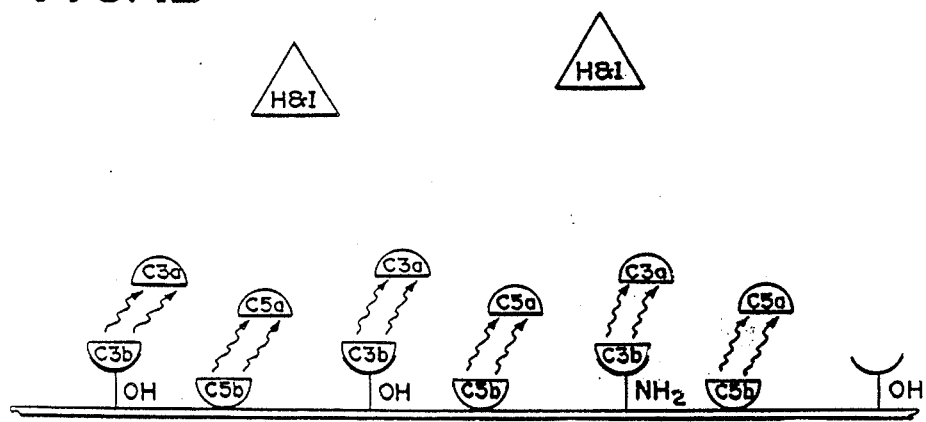
Figure 1C:
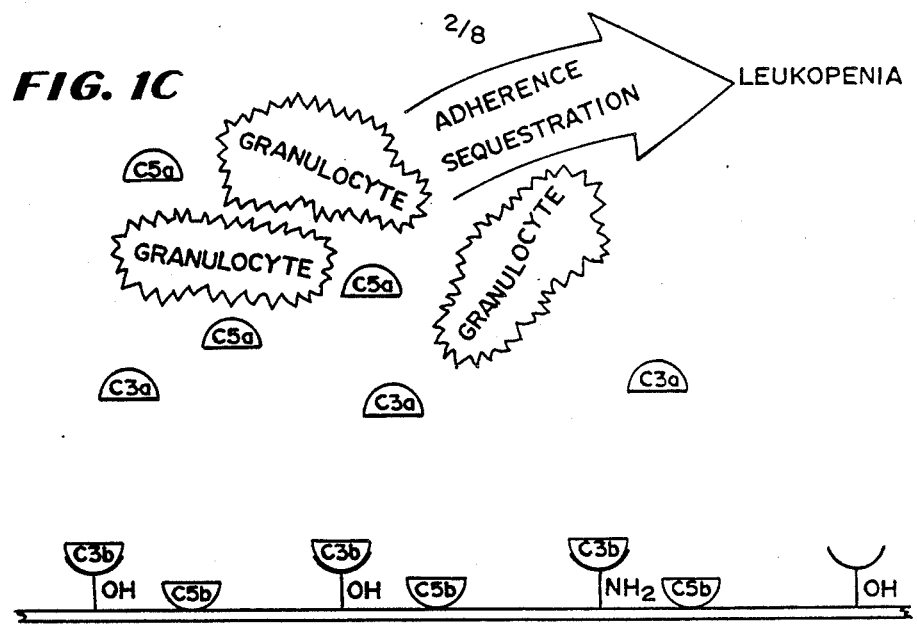

These nucleophilic groups 20 are known to be bio-reactive with certain proteins found in the human complement system. The bio-reactive nature of the nucleophilic groups has already been described, and is illustrated in FIGS. 1A to 1C.

The nucleophiles 20 shown in FIG. 3A are believed to differ in their bioreactivity. By their chemical nature, the amino groups ($NH_2$) are believed to be more nucleophilic, and thus more bio-reactive than the hydroxyl groups (OH). It is therefore believed that an amino group is more likely to bind acyl carbon atoms than a hydroxyl group.

In FIG. 3A, the material 16 is to be modified by reaction (indicated by arrows in FIG. 3A) with a material 22 selected from the group consisting of di-carboxylic anhydrides and acid halides. In FIG. 3A, maleic anhydride is the reaction material 22 used. The surface 18 of the cellulose membrane 16 after modification is shown diagrammatically in FIG. 3B. There, some of the bio-reactive surface nucleophilic groups 20 have been modified in a manner which blocks their natural characteristic of binding reactive acyl carbon atoms, like those associated with the complement C3b protein. The natural tendency of the material to activate the human complement system has thereby been reduced.

Figure 3B:
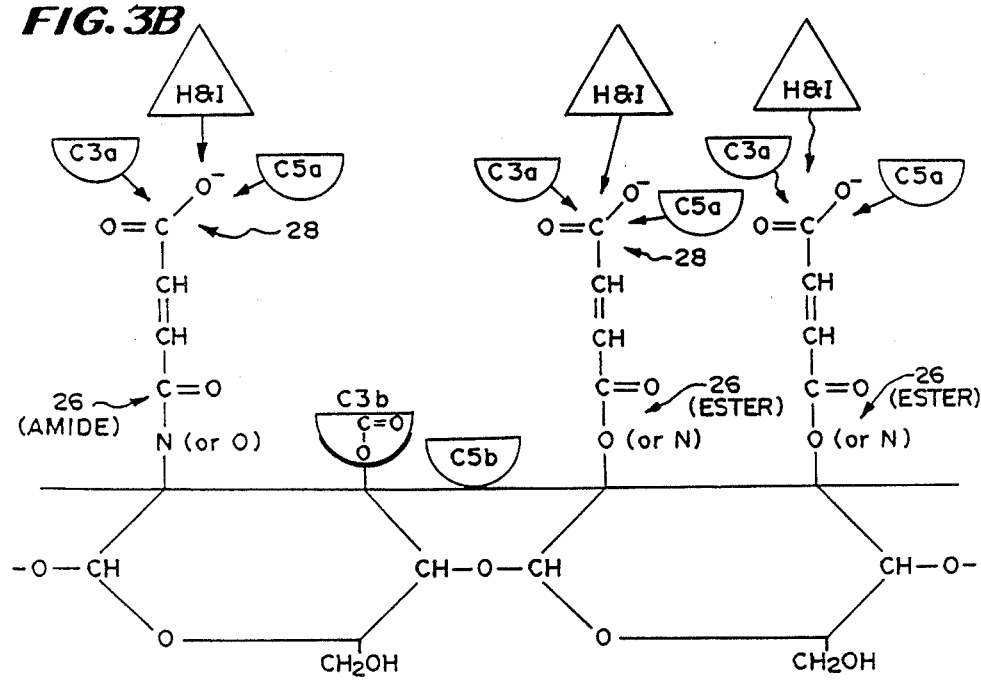

As shown in FIGS. 3A and 3B, the nucleophiles 20 have been modified with a material 22 which, like C3b, contains an activated carbonyl group (which is indicated by reference numeral 24 in FIG. 3A). Also like C3b, the material 22 forms a non-ether linkage (indicated by reference numeral 26 in FIG. 3B) with the nucleophile 20. However, unlike C3b, the material, in modifying the nucleophile, retains a free carboxyl (acid) group (indicated by reference numeral 28 in FIG. 3B) to impart a negative charge to the now modified nucleophilic site.

In addition to maleic anhydride, among the di-carboxylic acid anhydrides which also can be used to modify the nucleophilic groups are aconitic anhydride; 2, 3-dimethyl maleic anhydride; 2, 3-dichloromaleic anhydride; and 2, 3, 5, 6-benzene tetracarboxylic acid anhydride.

Among the acid halides which can be used to modify the nucleophilic groups are succinyl dichloride and glutaryl dichloride.

Table 1 summarizes the reaction between various di-carboxylic acid anhydrides and acid halides and regenerated cellulose and the resulting modified nucleophilic structure. Table 1 is intended to be representative of the type of materials and nature of reactions which embody the features of the invention. The contents of Table 1 are not to be considered all-inclusive. There are materials which will react with a nucleophilic group via a nucleophilic acyl substitution reaction to create non-ether linkages, while retaining a free carboxyl group, that are not listed in Table 1.

Furthermore, regenerated cellulose is not the only example of the nucleophilic material 16 which can be modified in accordance with this invention. Nucleophilic groups, as defined in this specification, are also associated with agarose derived materials, such as sepharose and cross-linked agarose. Such nucleophilic groups are also associated with amino polystyrene.

TABLE 1
REPRESENTATIVE REACTIONS BETWEEN REGENERATED CELLULOSE AND VARIOUS DI-CARBOXYLIC ACID ANHYDRIDES AND ACID HALIDES

DI-CARBOXYLIC ANHYDRIDES

1. MALEIC ANHYDRIDE

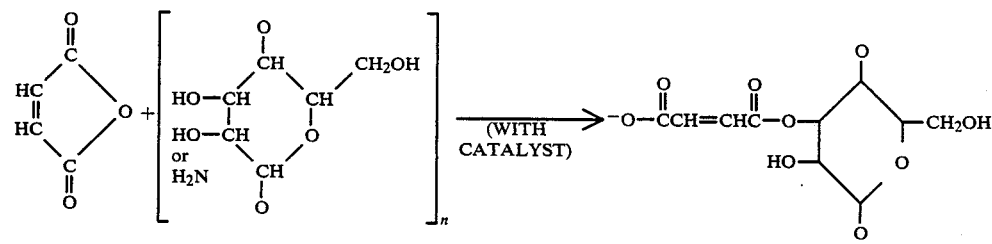

(Note: This will hereafter be referred to as "Regenerated Cellulose")

2. SUCCINIC ANHYDRIDE

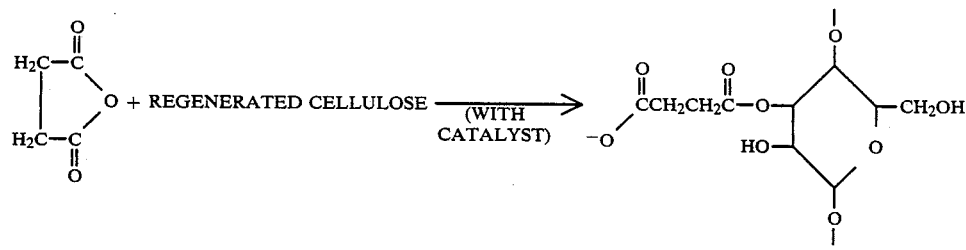

3. PHTHYALIC ANHYDRIDE

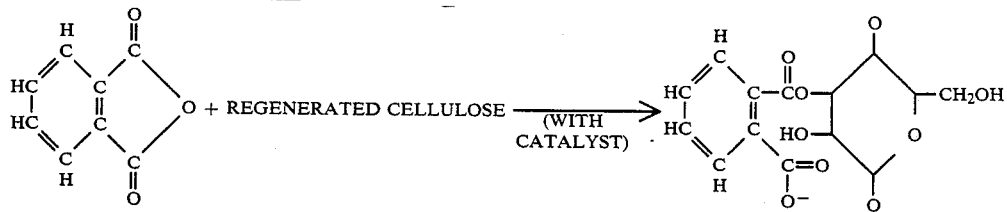

4. GLUTARIC ANHYDRIDE

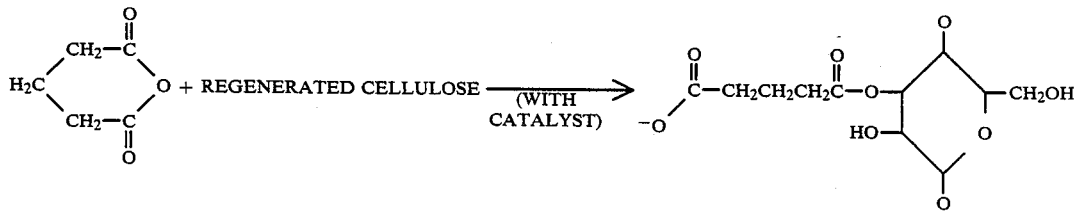

5. ACONITIC ANHYDRIDE

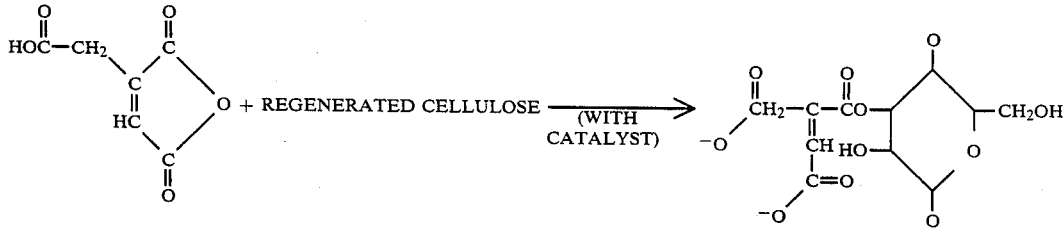

6. 2,3 DIMETHYL MALEIC ANHYDRIDE

TABLE 1-continued
REPRESENTATIVE REACTIONS BETWEEN REGENERATED CELLULOSE AND VARIOUS DI-CARBOXYLIC ACID ANHYDRIDES AND ACID HALIDES

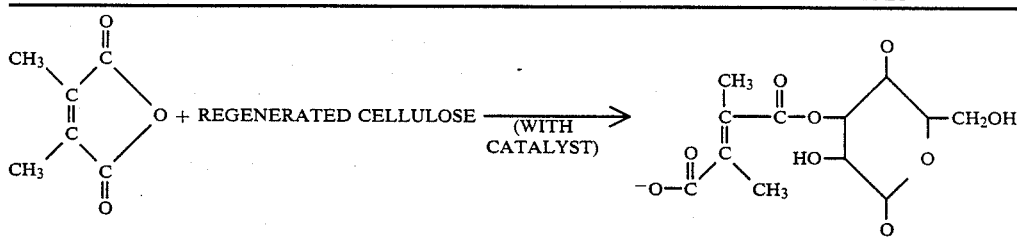

7. 2, 3, 5, 6 BENZENE TETRACARBOXYLIC ACID ANHYDRIDE

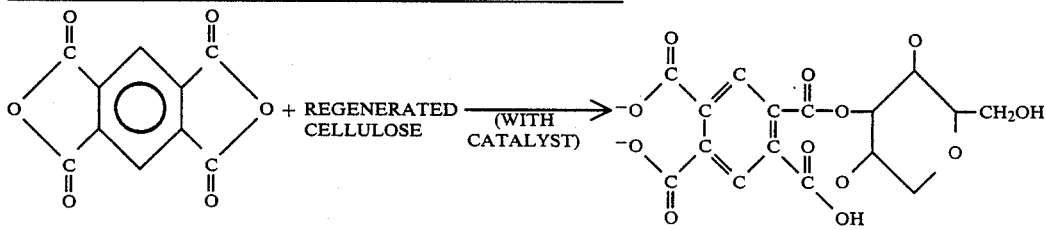

ACID HALIDES

1. SUCCINYL DI-CHLORIDE

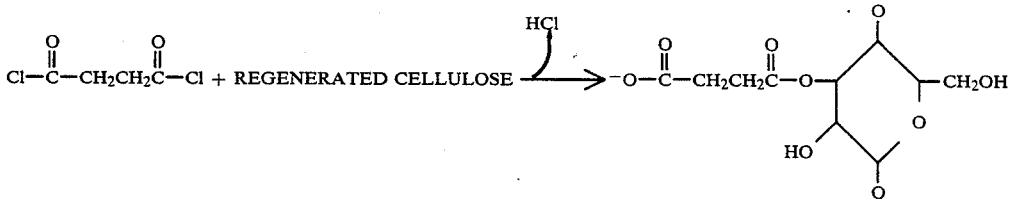

2. GLUTARYL DI-CHLORIDE

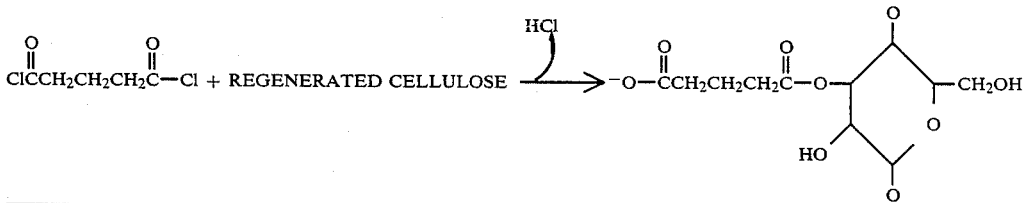

As more specifically shown in FIG. 3B, a non-ether amide linkage has been formed with the nucleophilic amino groups ($NH_2$), while a non-ether, ester linkage has been formed with the nucleophilic hydroxyl groups (OH).

In modifying the nucleophilic group 20, the nucleophilic material 16 is exposed to solutions of either di-carboxylic acid anhydride or acid halide and a suitable carrier. When a di-carboxylic acid anhydride solution is used, the presence of a catalyst is also preferred. Suitable catalysts include pyridine; triethylamine; N-N-dimethyl amino pyridine; and 4-pyrrolidinopyridine.

After a desired time, the reaction is stopped, using an aqueous wash. A subsequent drying step is also preferred.

The reaction time can be varied according to the concentration of the di-carboxylic acid solution or acid halide solution used, with more dilute solutions requiring a longer reaction time to obtain an optimal degree of modification. Given the same reaction material and the same concentration, however, control of the reaction time is believed to be important to optimize the beneficial effect of the invention.

More particularly, it has been observed that the effectiveness of the modification (in terms of percent reduction of complement activation realized) rises relatively rapidly with reaction time at the outset of the reaction and during an initial time period. However, the effectiveness then tends to level off with the reaction time. Surprisingly, with extended reaction time periods, the effectiveness has been observed to even diminish. This phenomenon is demonstrated in greater detail in Example 3 and is shown graphically in FIG. 5.

The polymer structure of the entire material 16 can be modified in accordance with the invention. However, only the surface 18 which is to come into contact the biological fluid need be treated to achieve the substantial benefits of the invention. This is because the invention is selective in blocking the most bio-reactive nucleophiles first, and relatively low levels of the reaction material can be used to accomplish this.

Reference is now made to the following Examples, where the benefits of the invention are demonstrated.

EXAMPLE 1

Cuprammonium rayon manufactured by Membrana AG (formerly Enka AG) and sold under the tradename "Cuprophan" was modified in accordance with the invention, using as the reaction material maleic anhydride, succinic anhydride, phthalic anhydride, and glutaric anhydride.

In each case, one (1) gram of the cuprammonium rayon material (in hollow fiber form) was mixed with a solution of the anhydride in tetrahydrofuran, with 3% (volume/volume) triethylamine added as a catalyst. 0.3M anhydride solutions of succinic anhydride and phthalic anhydride were used. More concentrated 3.5M solutions of maleic anhydride and glutaric anhydride were used.

The solution surrounding the material was stirred for one (1) hour at room temperature (22° C.), while the reaction took place. The modification was stopped by adding water. The modified cuprammonium rayon material was thoroughly washed with water, and then dried with an acetone wash.

Twenty-five (25) milligrams of each of the modified cuprammonium rayon materials were then placed in separate 1.5 milliliter tubes, where they were incubated with normal human plasma for one (1) hour at 37° C. Twenty-five (25) milligrams of unmodified cuprammonium rayon material were likewise incubated in a 1.5 milliliter tube with normal plasma to serve as a control.

The supernatant plasma in each tube was then analyzed for C3a and C5a anaphylatoxins by conventional radioimmunoassay (RIA) procedures (see, e.g., Hugli et al., "Biologically Active Peptides of Complement", *Immunoassays Clinical Laboratory Techniques for the 1980's*, New York, Alan R. Liss Inc., 1980, pp. 443–460).

The material itself was analyzed for C3b complement component by an immune based assay. In this assay, after removal of the supernatant plasma, the materials were washed three times with phosphate buffer saline (PBS). The washed materials were then incubated with 125 I-labeled rabbit anti-C3 (affinity purified antibody against human C3) diluted in PBS-Gelation containing 4% (vol/vol) of normal rabbit serum. After 60 minutes, the excess antibody was removed, and the materials were washed four times with 1 ml aliquots of PBS containing 0.1% Tween-20. The washed materials were then counted for bound antibody. Control tubes without material were treated identically and the CPMs obtained were employed to correct for nonspecific binding to the microfuge tube.

The results of the analyses are summarized in Table 2.

Table 2 demonstrates that the modification of normally nucleophilic materials (such as cuprammonium rayon) using a di-carboxylic acid anhydride results in a significantly reduced binding of C3b complement component to the surface of the material, when compared with unmodified (control) nucleophilic material. The degree to which complement binding was reduced was between about 50% for glutaric anhydride to about 92% for maleic anhydride.

Table 2 also demonstrates that there is also a significant reduction in the amount of C5a anaphylatoxin generated when exposed to the modified material, compared with the unmodified material. This degree of reduction ranged from 87.2% (for phthalic anhydride) up to 98.6% (for maleic anhydride). A similar significant reduction in the presence of C3a anaphylatoxin occurs.

TABLE 2
REDUCTION OF COMPLEMENT ACTIVATION WITH NUCLEOPHILIC MATERIAL MODIFIED WITH VARIOUS CARBOXYLIC ANHYDRIDES

| | C3b (n = 6) | | C3a (n = 6) | | | C5a (n = 6) | | |
|---|---|---|---|---|---|---|---|---|
| Material | Picomoles per 25 mg of Material | % Inhibition | Picomoles per ml of Plasma | uy/ml of Plasma | % Inhibition | Picomoles per ml of Plasma | ng/ml of Plasma | % Inhibition |
| Sample | | | | | | | | |
| 1. Cuprammonium rayon (control) | 132.5 | 0 | 385.2 | 3.467 | 0 | 13.56 | 112.54 | 0 |
| 2. Cuprammonium rayon modified with maleic anhydride (3.5 M Solution) | 11.0 | 91.7 | 3.56 | .032 | 99.1 | .18 | 1.58 | 98.6 |
| 3. Cuprammonium rayon modified with succinic anhydride (0.3 M Solution) | 44.3 | 65.6 | 60.44 | .544 | 84.3 | .56 | 4.64 | 95.9 |
| 4. Cuprammonium rayon modified with phthalic anhydride (0.3 M Solution) | 64.3 | 51.0 | 109.3 | .984 | 71.6 | 1.74 | 14.45 | 87.2 |
| 5. Cuprammonium rayon modified with glutaric anhydride (3.5 M Solution) | 46.8 | 63.5 | 52.6 | .474 | 86.3 | 1.41 | 11.67 | 89.6 |

As shown in Table 2, the percent reduction in the presence in C3a and C5a anaphylatoxins is greater than the percent reduction in the binding of C3b component. It is believed that the modified material not only serves to block the release of C3a/C5a anaphylatoxins (by blocking the binding of C3b), but also serves to bind the cationic C3a/C5a anaphylatoxins that may be generated by unmodified nucleophiles (due to the retention of the free carboxyl group). Example 2 further confirms this belief.

The greater effectiveness of maleic anhydride, when compared to the other carboxylic anhydrides used, is believed to be attributable to the use of a more concentrated solution during the one hour reaction period and to its increased reactivity when compared with the other anhydrides. It is believed that, by either extending the reaction period of the other anhydrides, and/or by increasing the concentrations used, comparable degrees of effectiveness can be obtained with the other anhydrides.

EXAMPLE 2

Cuprammonium rayon materials (in hollow fiber form) were modified with maleic anhydride as described in Example 1, except that different reaction times were used; namely 5 minutes, 20 minutes, 60 minutes, and 240 minutes.

Ten mg amounts of the materials were transferred to 1.5 ml microfuge tubes and incubated with varying concentrations of 125-I labeled C3a (40–200 nM) in a total volume of 0.5 ml. The tubes were incubated for 15 minutes, during which time the total CPM/tube was determined by counting. The unbound 125 I-3a (in supernatant) was removed by aspiration and the materials were washed three times with PBS. The percentage of bound material was determined by counting the residual radioactivity remaining in each tube. Control tubes without fiber were treated identically and the CPMs obtained were employed to correct for nonspecific binding to the microfuge tube.

The results are summarized in Table 3.

TABLE 3
BINDING OF C3a ANAPHALOTOXIN TO NUCLEOPHILIC MATERIAL MODIFIED WITH MALEIC ANAYDRIDE

| MATERIAL | % C3a Bound |
| --- | --- |
| Cuprammonium Rayon (Control) | 4.0 |
| Cuprammonium Rayon modified with maleic anhydride for: | |
| 5 minutes | 9.0 |
| 20 minutes | 10.6 |
| 60 minutes | 10.9 |
| 240 minutes | 5.8 |

Table 3 demonstrates that material modified in accordance with the invention does bind free C3a anaphylatoxins. Table 3 also demonstrates that the degree of binding increases with reaction time up to finite time, then decreases.

EXAMPLE 3

Cuprammonium rayon material (in hollow fiber form) were modified with maleic anhydride as described in Example 1, using the following reaction times: 5 minutes; 10 minutes; 20 minutes; 60 minutes; 240 minutes; and 18 hours.

The materials were incubated in normal human plasma, also as described in Example 1, for one (1) hour at 37° C.

C3b; C3a; and C5a were analyzed using the methods described in Example 1.

A portion of the modified fiber (0.5 grams) was also treated separately as follows. The fibers were incubated with 0.5N HCl to protonate all the carboxyl groups on the fiber. The fibers were then washed extensively with water to remove excess acid and then suspended in 50 ml. of 0.1N NaCl and titrated with 0.5N NaOH. This titrimetric analysis permitted determination of the charge density (milliequivalents $COO^-$/gm fiber as assessed by milliEq of NaOH added/gm fiber), as well as the degree of substitution.

Table 4 summarizes the results.

TABLE 4
INHIBITION OF COMPLEMENT ACTIVATION WITH MALEIC ANHYDRIDE MODIFIED CUPRAMMONIUM RAYON

| Material | C3b (n = 5) | | C3a (n = 6) | | | C5a (n = 6) | | | MilliEq of NaOH/gm of Material | Degree of Substitution (Normalized to Control*) |
| --- | --- | --- | --- | --- | --- | --- | --- | --- | --- | --- |
| | Picomoles per 25 mg of material | % Inhibition | Picomoles per 1.0 ml of Plasma | ug/ml of plasma | % Inhibition | Picomoles per 1.0 ml of plasma | ng/ml of plasma | % Inhibition | | |
| Cuprammonium | 145 | 0 | 290 | 2.61 | 0 | 11.86 | 98.44 | 0 | 03 | 0 |
| Cuprammonium rayon modified with maleic anhydride, with time of reaction | | | | | | | | | | |
| 5 minutes | 56.6 | 61 | 42 | .378 | 85.5 | 4.3 | 35.69 | 64.0 | .14 | 0.018 |
| 10 minutes | 39.9 | 72.4 | 22.1 | .199 | 92.3 | 2.2 | 18.26 | 81.8 | .08 | 0.008 |
| 20 minutes | 21.0 | 85.5 | 12.7 | .114 | 95.6 | 2.1 | 17.43 | 82.1 | .07 | 0.007 |
| 60 minutes | 13.8 | 90.5 | 17.2 | .155 | 94.1 | 0.6 | 4.98 | 95.0 | .035 | 0.001 |
| 240 minutes | 10.3 | 92.9 | 5.8 | .052 | 98.0 | 1.1 | 9.13 | 90.8 | .045 | 0.002 |
| 18 hours | 20.7 | 85.8 | 19.04 | .171 | 93.4 | 0.55 | 4.57 | 95.4 | .025 | 0 |

NOTE: The degree of substitution represents the Moles of Maleic Acid per total Moles of Glucose in the material.

Table 4 demonstrates that, with a 3.5M solution of maleic anhydride, a reaction time of about 60 minutes is sufficient to get the desired degree of inhibition, both with respect to the binding of C3b and the reduction in the amount of C3a and C5a anaphylatoxins. Up to about 60 minutes, the degree of inhibition generally increases with increases in the reaction time.

Figure 5:
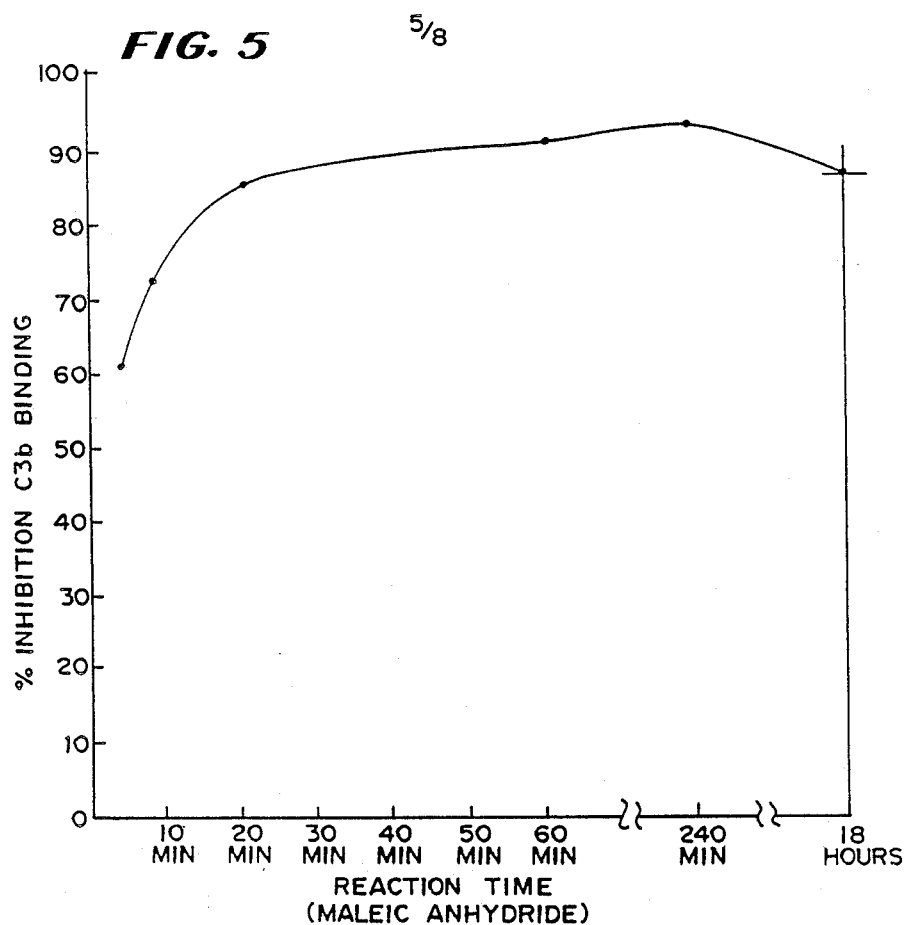
FIG. 5 is a graph demonstrating the relationship between the reaction time involved in modifying materials in accordance with the invention and the inhibition of binding of complement component C3b.

FIG. 5 is a graph which plots the relationship of degree inhibition of C3b deposition with reaction time. After about 60 minutes, the degree of inhibition does not appreciably increase. In fact, after prolonged reaction time, the degree of inhibition is sometimes observed to decrease. This data demonstrates the importance of controlling the reaction time.

Table 4 also demonstrates that the degree of actual substitution brought about by treating the material in accordance with the invention is relatively small. In this specification, the term "Degree of Substitution" refers to the Moles of reaction material which have become associated (i.e., bound) per total Moles of backbone polymer in the material (which, in the case of regenerated cuprammonium, is glucose). It is a measure of the number of nucleophiles which have been modified in accordance with the invention.

Table 4 demonstrates that, by modifying materials in accordance with the present invention, which selectively blocks the most bio-reactive nucleophiles, a relatively small degree of substitution can obtain significant results.

Table 4 also demonstrates that the amount of negative charge on the surface of the material (as measured by the Milli Ed of NaOH/gm of material) triples after five (5) minutes of modification, but then returns to control values after about 60 minutes. However, the percent inhibition of the cationic C3a and C5a anaphylatoxins still remains significant. This is considered a surprising and unexpected result.

Figure 6:
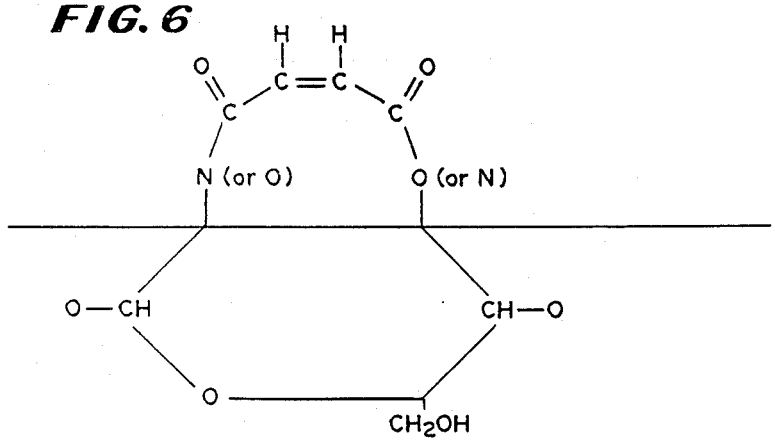
FIG. 6 is a diagrammatic depiction of regenerated cellulose material after treatment in accordance with the invention, showing a theoretical cross-linking between one modified nucleophilic group and an unmodified nucleophilic group.

One hypothesis explaining this observation is that the group linked to some of the modified nucleophiles may actually bend over and attach itself to an adjacent unmodified nucleophiles, as is shown in FIG. 6. In this circumstance, the negative charge of the modified nucleophile will disappear; however, the attachment to the adjacent nucleophile (creating a diester linkage) results in an overall reduction in the number of bio-reactive sites. This will prevent the binding of C3*b* proteins, leading to the observed inhibition of C3*a* and C5*a* anaphylatoxins.

An alternative hypothesis, also consistent with the titration data presented in Table 4, is that, the prolonged reaction times, the anhydride modifies an extractable material found in cellulose and, together with the extractable material, is washed away during the washing step.

For example, substances called lymulus amaebocyte lysate-reactive materials (LAL-RM) are low molecular weight carbohydrate polymers that are found in cellulose and can be extracted. LAL-RM could be modified by treatment in accordance with the invention. More particularly, it is possible that the reaction materials used in accordance with the invention, such as maleic anhydride, convert LAL-RM to a form that is more easily extracted from cellulose by conventional aqueous washing procedures. In this case, both the amount of maleic anhydride and potentially extractable LAL-RM left in the cellulose would diminish as reaction times are prolonged, because more of the anhydride-converted LAL-RM would be washed away during the washing step.

In an attempt to distinguish between the two possibilities described above (i.e., diester formation, shown in FIG. 6, vs. removal of modified LAL-RM), the experiment described in Example 3 was repeated with [$^{14}C$] labeled maleic anhydride added to the reaction mixture.

In this experiment, 0.5 gms. of cellulose (plus 1 stir bar); 3.5 ml of 3.5M maleic anhydride in tetrahydrofuran; and 10 mCi (microcurie) of [$^{14}C$] maleic anhydride were added to five separate glass vials, with 0.105 ml of triethylamine added to initiate the reaction.

After 5, 20, 60, and 240 minutes, and 22 hours, the reaction was stopped by addition of 0.3 ml of water. The reaction solution was removed, and the fibers were washed with five 2 ml aliquots of 50% aqueous acetone, followed by 500 ml of water. The fibers were dried with acetone and stored in the capped glass vials.

To analyze for the presence of the [$^{14}C$] maleic anhydride, 100 mg of the treated fiber was added to a vial, and 15 ml of conventional scintilation cocktail was added. The vials were counted in a Packard scintilation spectrophotometer. The material was analyzed for C3*b*, C3*a* and C5*a* as described before, and also were counted to ascertain the amount of [$^{14}C$] maleic acid present on each group of fibers.

The data is summarized in Table 5.

Table 5 demonstrates (in the last column) that the initial increase in CPM/gm (during the first five minutes of reaction time) is followed by decrease in CPM values. This trend is consistent with previous data (Table 4, in the milliEq NaOH column). This suggests that some of the maleic acid (and perhaps some LAL-RM) is removed from the fiber during prolonged reaction times and is washed away in a subsequent washing step.

The C3*b*, C3*a*, and C5*a* data in Table 5 also follows the trend noted before and shown in FIG. 5; namely, that as the reaction time is prolonged, the desired effects of the modification increase, then level off, and, in time, will even decrease. The criticality of controlling the reaction time is again demonstrated.

TABLE 5

INHIBITION OF COMPLEMENT ACTIVATION WITH MALEIC ANHYDRIDE MODIFIED CUPRAMMONIUM RAYON (USING $^{14}C$-MALEIC ANHYDRIDE)

| | C3b (n = 5) | | C3a (n = 6) | | | C5a (n = 6) | | | |
|---|---|---|---|---|---|---|---|---|---|
| Material | Picomoles per 25 mg of material | % Inhibition | Picomoles per 1.0 ml of Plasma | ug/ml of plasma | % Inhibition | Picomoles per 1.0 ml of plasma | ng/ml of plasma | % Inhibition | CPM/gm |
| Cuprammonium | 145 | 0 | 290 | 2.61 | 0 | 11.86 | 98.44 | 0 | 0 |
| Cuprammonium rayon modified with maleic anhydride, with time of reaction | | | | | | | | | |
| 5 minutes | 56.6 | 61 | 42 | .378 | 85.5 | 4.3 | 35.69 | 64.0 | 9,430 |
| 20 minutes | 21.0 | 85.5 | 12.7 | .114 | 95.6 | 2.1 | 17.43 | 82.1 | 4,597 |
| 60 minutes | 13.8 | 90.5 | 17.2 | .155 | 94.1 | 0.6 | 4.98 | 95.0 | 4,047 |
| 240 minutes | 10.3 | 92.9 | 5.8 | .052 | 98.0 | 1.1 | 9.13 | 90.8 | 3,2 |
| 22 hours | 20.7 | 85.8 | 19.04 | .171 | 93.4 | 0.55 | 4.57 | 95.4 | 2,767 |

Another aspect of the present invention is the ability of materials treated in accordance with the invention to bind Beta-2-microglobulin and other poorly dialyzed molecules in the 1000 to 2000 molecular weight range. This feature of the invention is demonstrated in Example 4.

EXAMPLE 4

Regenerated cellulose materials were treated with maleic anhydride in accordance with Example 1, with the reaction times varied from 10 to 240 minutes.

After the reaction, the cellulose materials were cut into 0.5–2.00 mm pieces and washed with PBS, water and acetone. Five mg amounts of the material were transferred to 1.5 ml microfuge tubes and incubated with 0.5 ml of a solution containing 125-I labeled Beta-2-microglobulin (100,000 CPM/ml). The tubes were counted to determine the total CPM per tube. After 15 minutes, the fluid phase Beta-2-microglobulin was removed by aspiration and the materials were washed three times with 1 ml aliquots of PBS. The percentage of bound material was determined by counting the residual radioactivity remaining in the tube. Control tubes without material were treated identically and the CPM obtained were used to correct for nonspecific binding to the microfuge tube.

The results are summarized in Table 6.

TABLE 6
BINDING OF BETA-2 MICROGLOBULIN TO REGENERATED CELLULOSE MODIFIED WITH MALEIC ANHYDRIDE

|  | % Reduction |
|---|---|
| Control | .16% |
| Reaction time: |  |
| 5 minutes | .40% |
| 20 minutes | .24% |
| 60 minutes | .28% |
| 240 minutes | .25% |

Table 6 demonstrates that nucleophilic material treated in accordance with the invention binds Beta-2-microglobulin.

Figure 7:
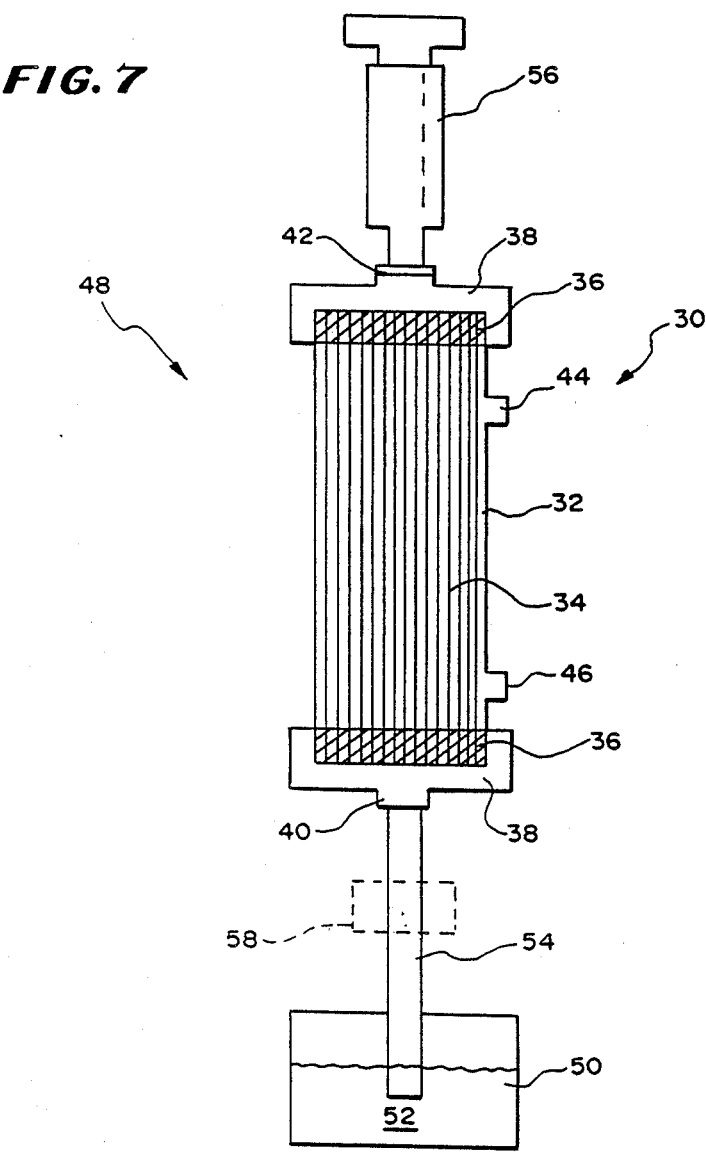
FIG. 7 is a conventional finished dialyzer in association with a treatment system which embodies the features of the invention.

Reference is now made to FIG. 7, where a hollow fiber dialyzer 30 is shown. The dialyzer 30 includes a case 32 housing a bundle 34 of conventional cuprammonium rayon fibers, as manufactured by Membrana AG and sold under the tradename "Cuprophan". The ends of the fiber bundle 34 are encapsulated with a polyurethane sealing compound 36 and each covered with an end cap 38.

Inlet and outlet ports 40 and 42 are formed on the end caps 38 for conveying blood into an out of the interior bores of the fiber bundle 34. Dialysate inlet and outlet ports 44 and 46 are formed on the case 32.

Dialyzers of the configuration shown in FIG. 7 are commercially available and are sold, for example, by Travenol Laboratories, Inc. under the trademark CF® Capillary Flow Dialyzers.

As is also shown in FIG. 7, a finished medical device, such as the dialyzer 30, can be treated in accordance with the invention to improve its biocompatibility.

A system 48 for treating the finished dialyzer 30 in accordance with the invention is shown in FIG. 7. The system 48 includes a reservoir 50 for holding the treatment material 52 and a conduit 54 which conveys the material 52 into the dialyzer 30 via the inlet port 40. A negative pressure generating device, shown as a syringe 56 in FIG. 7, is attached to the other port 42. The syringe 56 draws the treatment material 52 into and through the bores of the hollow fiber bundle 34.

Alternatively, a positive pressure generating device 58 (shown in phantom lines in FIG. 7) can be used to introduce treatment material 52 into the dialyzer 30.

Figure 8A:
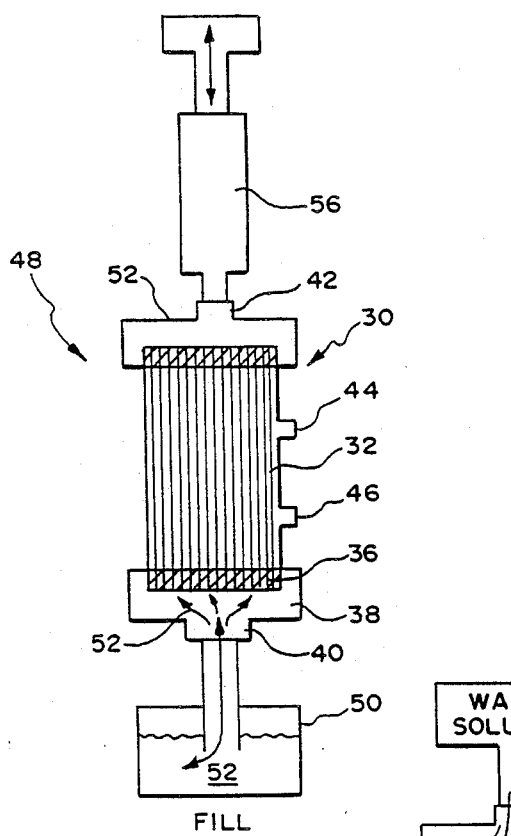
FIGS. 8A to 8C illustrate, in diagrammatic form, the operation of the treatment system shown in FIG. 7.
Figure 8B:
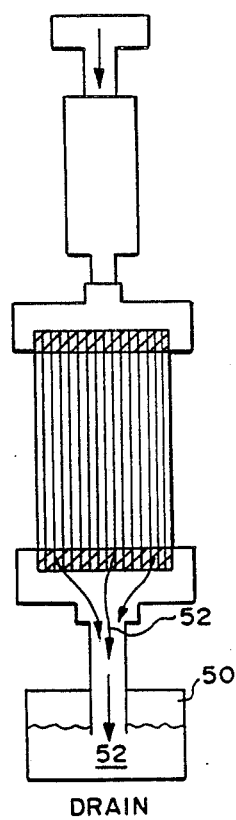
Figure 8C:
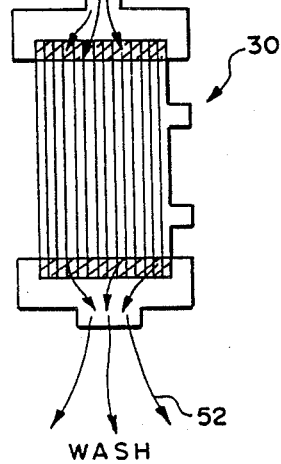

The use of the system 48 in treating the dialyzer is shown schematically in FIGS. 8A to 8C.

In FIG. 8A, suction is applied by the syringe 56 to draw the treatment material 52 into the bores of the fiber bundle 34. Preferably, the material 52 is successively sucked into the expelled out of the dialyzer 30 several times (as indicated by the double-headed arrow in FIG. 8A) to rid the dialyzer 30 of air bubbles and assure that the bores of the fibers 34 are filled with the treatment material 52.

The treatment material 52 is allowed to dwell within the bores of the fiber bundle 34 for a prescribed reaction period. The length of the reaction time is a function of the concentration and reactivity of the particular treatment material used, as before described in this specification.

As shown in FIG. 8B, after the prescribed reaction period, the treatment material 52 is expelled from the dialyzer 30.

As shown in FIG. 8C, the residue treatment material 52 is then washed from the dialyzer 30 using water, or alcohol, or a suitable compatible solvent, or a combination thereof.

As can be seen, the system 48 localizes the treatment to the surface of the interior bores of the fiber bundle 34. The remaining material of the fiber bundle 34 is believed to be virtually untreated.

The treatment material 52 can vary. In the illustrated and preferred embodiment, the material 52 is selected from the group consisting of di-carboxylic acid anhydrides and acid halides.

In one preferred adaptation, the treatment material 52 is carried by an enert carrier, such as a chlorofluorocarbon; for example, trichlorofluoromethane; 1,1,2-trichloro-1,2,2-trifluoroethane; 1,1,2,2-tetra-chloro-1,2-difluorethane or the like, alone or in combination with a material capable of forming an azeotrope, such as alcohols, ketones, esters, and ethers. Such materials are sold by DuPont under the trademark "Freon". Chlorofluorocarbon materials have also been widely used in the manufacture of cellulosic materials.

EXAMPLE 5

A treatment system as shown in FIGS. 7 and 8 was constructed. Prototype dialyzers were constructed, using conventional "Cupraphan" cuprammonium rayon fibers.

Maleic anhydride was dissolved in 10 ml of Freon TF chlorofluorocarbon to a concentration of 5.65 mg/ml (equal to 57.6 mM) and placed in a reservoir along with 300 ul of the catalyst triethylamine (TEA). The maleic anhydride/TEA/Freon TF mixture was drawn up into a prototype dialyzer by suction applied with a syringe. The mixture was alternatively sucked into and expelled out of the dialyzer several times in order to rid the dialyzer of air bubbles and assure that the lumens of all of the fibers were filled.

The dialyzer was then incubated at room temperature for about 2 hours, with the Maleic Anhydride/TEA/Freon TF mixture occupying the lumens of the fibers. During this dwell period, the treatment mixture remained within the bores of the fiber and was not observed to leak or seep through the fibers into the surrounding case. The maleic anhydride/TEA/Freon TF mixture was then expelled from the dialyzer. The dialyzer was then washed with about 10 ml of Freon TF, followed by 300 ml of water, 100 ml of PBS, and finally with 100 ml of water.

A control dialyzer was treated identically, except that no maleic anhydride was added to the Freon TF/TEA mixture.

Four (4) ml of normal human plasma was sucked up into the treated dialyzer and the control dialyzer. Both dialyzers were placed in a 37° C. oven for 60 minutes. The plasma from inside the dialyzers was collected and assayed for complement activation by C3a/C5a RIA, using the test procedures set forth in Example 1. The results are summarized in Table 7.

TABLE 7
INHIBITION OF COMPLEMENT ACTIVATION WITH MALEIC ANHYDRIDE APPLIED WITH FREON TF AND TEA IN A FINISHED DIALYZER.

| DIALYZER | C3a | | C5a | |
| --- | --- | --- | --- | --- |
|  | ug/ml of Plasma | % Inhibition | ng/Ml of plasma | % Inhibition |
| Control | 9.325 | — | 341.42 | — |

TABLE 7-continued

INHIBITION OF COMPLEMENT ACTIVATION WITH MALEIC ANHYDRIDE APPLIED WITH FREON TF AND TEA IN A FINISHED DIALYZER.

| DIALYZER | C3a | | C5a | |
|---|---|---|---|---|
| | ug/ml of Plasma | % Inhibition | ng/Ml of plasma | % Inhibition |
| Modified with Maleic Anhydride | 1.265 | 86.5 | 33.5 | 90.2 |

Table 7 demonstrates the effectiveness of the invention in treating a finished medical product.

Table 7 also demonstrates the effectiveness of the invention in selectively localizing and controlling the extent of modification. In particular, only the surface where contact with biological liquids is to occur need be selectively treated to achieve significant reductions in complement activation.

In the case of hollow fiber materials, such as shown in FIGS. 7 and 8, a reactive lumen fluid can be introduced which selectively modifies the surface characteristics of the hollow fiber only along its interior bore. In the case of a fluid path defined between two flat sheets of material, a comparable localized modification can be accomplished by passing the reactive fluid only along the fluid path.

The reactive fluid can be introduced into the hollow fiber bores or into any intended fluid path, regardless of its configuration, after manufacture, before or after being incorporated into a finished medical device.

In accordance with another aspect of the invention, a reactive lumen fluid can also be introduced during the manufacture of the hollow fibers.

Figure 9:
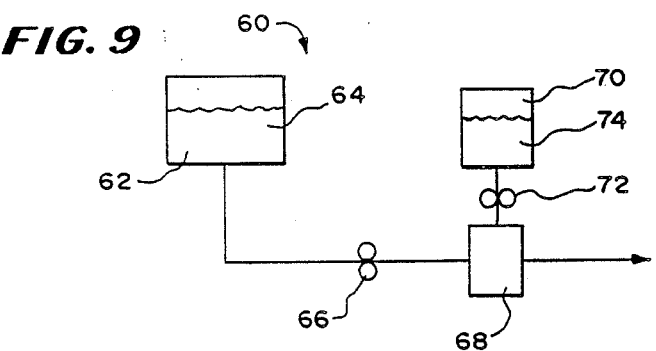
FIG. 9 is a system, shown in diagrammatic form, of forming material into hollow fiber form in accordance with the invention.

In this respect, reference is now made to FIG. 9. There, a system 60 for forming material into hollow fiber form is shown. In accordance with the invention, as the hollow fiber is being formed, the system 60 simultaneously alters the surface characteristics of the formed material along the interior bore of the fiber.

Generally the system 60 includes a first reservoir 62 where an extrusion solution or melt 64 is contained. A pump 66 conveys the extrusion solution into an extrusion die 68, which forms the solution into a tubular shape.

The system 60 also includes a second reservoir 70 and associated pump 72. A lumen fluid 74 is contained in the second reservoir 70. The pump 72 conveys the lumen fluid 74 into the interior region of the tubular shape as it is being formed.

The system 60 as just generally described is conventional in its configuration and operation and can be used to form various diverse materials into tubular shapes.

In accordance with the invention, the system 60 differs from conventional hollow fiber extrusion systems in that the lumen fluid 74 used by the system 60 includes a constituent which, when in contact with the mateiral being formed, reacts to alter the surface characteristics of the formed material. Because the reactive lumen fluid 74 is conveyed only into the interior region of the tubular shape, essentially only the surface characteristics of the interior bore will be effected.

In the preferred embodiment, the material of the extrusion solution 64 contains nucleophilic groups. In this context, the reactive lumen fluid 74 includes a constituent which covalently reacts with the nucleophilic groups to improve the overall biocompatibility of the formed hollow fiber.

Figure 10:
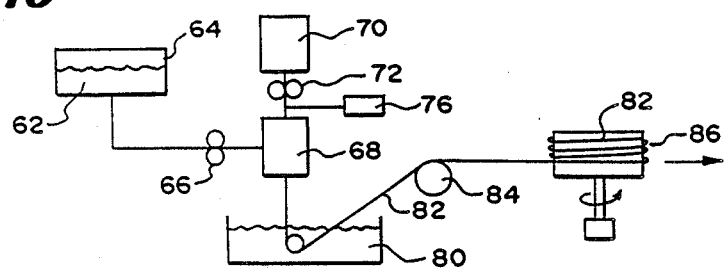
FIGS. 10 and 11 A and B are a system, shown in diagrammatic form, of forming cellulosic material into hollow fiber form in accordance with the invention.

In FIG. 10, an adaptation of the system 60 to manufacture cellulosic materials into hollow fiber form is shown. Elements common to FIG. 9 are given the same reference numerals.

The system 60 shown in FIG. 10, except as altered in accordance with the invention, forms cellulosic materials into hollow fibers following the process disclosed in, for example, German Pat. No. 864,904, as well as in U.S. Pat. No. 4,276,173.

Cotton linters are added slowly to the first reservoir 62, with stirring, which also contains an aqueous solution of copper tetrammine hydroxide. A highly viscous cellulose solution 64 is formed containing about 9.5% cellulose and having a cellulose to copper ratio of 2.35 ("CAC Solution").

The CAC solution is pumped from the reservoir 62 via the metering pump 66 into the extrusion die 68, which forms the CAC solution into a tubular shape.

Simultaneously, the lumen fluid stream 74 is introduced via metering pump 72 from the reservoir 70 into the central region of the tubular CAC solution stream.

Conventionally, the lumen fluid 74 contains an inactive organic liquid which is immiscible with the cellulose, for example, isopropyl myristate (IPM). This liquid forms the interior bore of the fiber.

In accordance with the invention, the lumen fluid 79 contains, in addition to the immiscible constituent, a second constituent which reacts with the cellulosic material to change its surface characteristics. In the illustrated embodiment, the second constituent is selected from the group consisting of di-carboxylic acid anhydrides and acid halides.

A second core fluid stream 76 contains, when necessary, a catalyst 78 for the reactive constituent of the lumen fluid 74.

The tubular extrudate enters an aqueous sodium hydroxide bath 80, which coagulates the CAC Solution to form a self-supporting hollow fiber 82. Still resident within the formed fiber 82 is the reactive lumen fluid 74. The fiber 82 is continuously pulled from the bath 80 by means of a take up wheel 84. The fiber 82 is wound onto a two-prong fork 86.

Figure 11A:
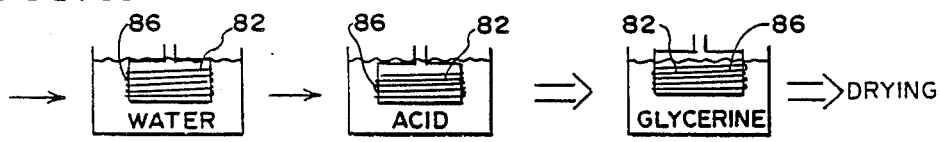
Figure 11B:
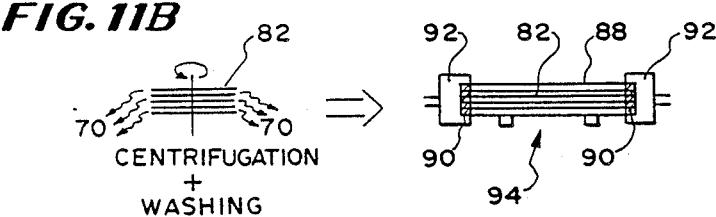

As shown in FIG. 11A, the fiber 82 on the winding fork 86 is first immersed in water to remove surface sodium hydroxide, and is then immersed into an acid solution to remove copper. The fiber 82 is then rinsed again with water, immersed in glycerol solution, and then dried in an oven. During these steps, the reactive lumen fluid 74 still resides within the fiber bore.

The dried fibers 82 are next cut from the winding forks 86. The reactive lumen fluid 74 is now removed by centrifugation, followed by washing in Freon TF.

The fibers 82 are placed in a case 88 and encapsulated at the ends with a conventional polyurethane sealing compound 90, which is subsequently cut to expose the lumens of the fibers 82. Finally, end caps 92 are fitted on the case 88 and a final wash is performed, again with Freon TF.

The resulting dialyzer 94 contains hollow fibers 82 which have been selectively modified during manufacture to alter the surface characteristics of the interior bores.

EXAMPLE 6

Dialyzers were manufactured in the manner just described, using a reactive lumen fluid having isopropyl myristate as the first constituent and maleic anhydride as the second constituent. The two constituents were combined to create a saturated solution (approximately 200 mM) of maleic anhydride in the isopropyl myristate at room temperature. In some cases, triethylamine (TEA) was used as a catalyst. The dialyzers were washed with 10 ml of PBS and then filled with normal human plasma using positive pressure to inject the plasma into the bores of the fibers. The excess plasma was collected and served as a control. The dialyzers and associated excess plasma were incubated at 37° C. for one hour. The plasma was collected from inside the dialyzers and analyzed, along with the control plasma, for C3a and C5a using RIA, following the technique described in Example 1.

The results are summarized in Table 8.

TABLE 8

MODIFICATION OF CELLULOSIC HOLLOW FIBERS INCORPORATING MALEIC ANHYDRIDE INTO THE LUMEN FLUID.

| | C3a | | C5a | |
|---|---|---|---|---|
| DIALYZER | ug/ml of Plasma | % Inhibition | ng/ml of plasma | % Inhibition |
| 1. Control | 3.809 | — | 112.42 | — |
| 2. Mal Only | 0.164 | 95.7 | 4.4 | 96.1 |
| 3. Mal/.1% TEA | 0.096 | 97.5 | 12.8 | 88.6 |
| 4. Mal/.5% TEA | 0.038 | 99.0 | 12.5 | 88.9 |
| 5. Mal/1.0% TEA | 0.160 | 95.8 | 66.2 | 41.1 |

Table 8 demonstrates that materials can be formed into hollow fibers while the surface characteristics of fiber bores are simultaneously modified.

The data in Table 8 demonstrates several surprising observations. First, in this application of the invention, the catalyst, in this case TEA, was not a necessary constituent of the reaction mixture as demonstrated by line 2 of Table 8. This may be attributed to the basic nature of the cuprammonium melt. Some component of the cuprammonium mixture (e.g., $NH_3$) may act as an efficient catalyst. Second, not only is the TEA unnecessary in this application of the invention, its inclusion seems to lead to lower levels of inhibition of C5a (i.e., higher levels of C5a) even though C3a levels do not change significantly. Since C5a is less cationic than C3a, this observation might be explained by suggesting a lower degree of substitution and, therefore, a lower negative charge density on the cellulose with the 1.0% TEA solution.

COMPARISON WITH OTHER MODIFICATION METHODS

Figure 4A:
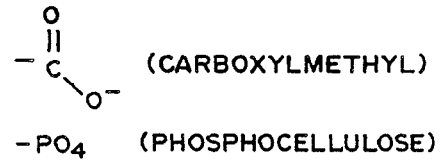
FIGS. 4A and 4B are diagrammatic depictions of regenerated cellulose material as modified by others and not in accordance with the invention.
Figure 4A:
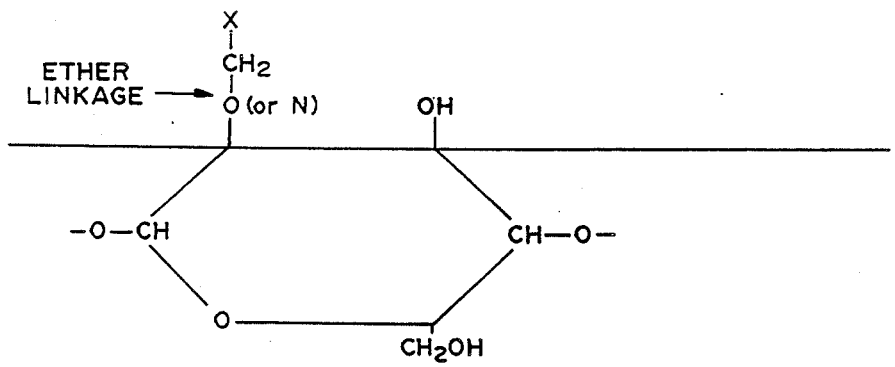

The modification made in accordance with this invention differs significantly in terms of resulting structure and effect from other cellulose modification methods. In FIG. 4A, for example, the modified nucleophile structure resulting from the bulk blending process described in European Application 0 272 437 is depicted. As seen in FIG. 4A, the modification results in the formation of an ether linkage (O—$CH_2$), not in the amide or ester linkage created by the reaction of the invention. The observed reductions in C3a concentrations in the presence of the modified nucleophiles (when compared to pure cellulose membrane) were 69% (European Application, Example 2); 73% (European Application, Example 3); and 77% (European Application, Example 4). The C3a reductions observed when the nucleophiles are modified in accordance with the present invention are generally greater (see, e.g., Tables 2, 3, and 4 of this Specification).

Figure 4B:
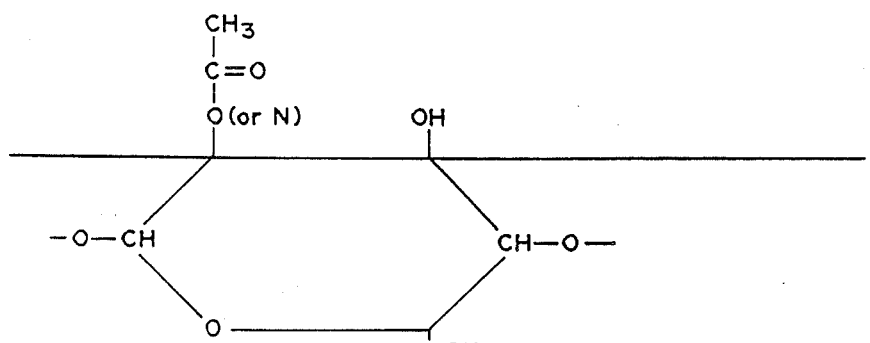

In FIG. 4B, the modified nucleophile structure of cellulose acetate is depicted. As can be seen, while the modified nucleophile includes an ester linkage (O—C=O), no free carboxyl group is retained to impart a negative charge to the surface. As reported in Chenoweth, "Complement Activation During Hemodialysis: Clinical Observations, Proposed Mechanisms, and Theoretical Implications", *Artificial Organs,* 8(3) 1984, pp. 281 to 287, at p. 283–284, the observed reductions in C3a concentrations using cellulose acetate, after thirty minutes were about 50 to 60%, compared with pure cellulose. Again, the reductions observed when the nucleophiles are modified in accordance with the present invention are greater.

SUMMARY

In summary, the invention provides a modified nucleophilic material having improved biocompatibility. The modification employs a material having an activated carbonyl group which, via a nucleophilic acyl substitution reaction mechanism, creates a non-ether linkage while retaining a free carboxyl group. The modification blocks the most highly reactive nucleophiles. It simultaneously introduces a negative charge which favors the binding of Factors H&I to limit complement activation. The negative charge also binds cationic C3a and C5a anaphylatoxins to limit patient exposure to these bio-reactive polypeptides.

The modification also binds Beta-2-microglobulin and similar, poorly dialyzed molecules to the material.

The invention is especially well suited for use with regenerated cellulose membranes, offering significantly improved biocompatibility without significantly increasing in manufacturing costs. The invention allows finished dialyzers to be treated with relatively small amounts of reactive materials to achieve significant reductions in complement activation. The invention also allows materials to be formed into hollow fibers while simultaneously altering the surface characteristics of the fiber bores.

Various features and advantages of the invention are set forth in the following claims.

We claim:

1. A method of forming a material having nucleophilic groups into hollow fiber form while selectively modifying the surface characteristics of the material along the interior bore of the hollow fiber to prevent complement activation and bind beta 2 microglobulin, said method comprising the steps of forming the material into a tubular shape around a lumen fluid which serves as a central core around which said fiber is formed and which fluid includes a constituent having an activated carbonyl group which reacts chemically with the material in a predetermined fashion as the fiber is being formed.

2. A method according to claim 1 wherein during said forming step, the material is extruded through a die.

3. A method according to claim 2 wherein, during said lumen fluid introduction step, the lumen fluid includes a constituent which is immiscible with the material and which forms the interior bore of the hollow fiber.

4. A method according to claim 1 wherein, during said lumen fluid introduction step, the lumen fluid includes a constituent which is immiscible with the material and which forms the interior bore of the hollow fiber.

5. A method according to claim 1 and further including the step of removing the lumen fluid from the interior region of the tubular shape.

6. A method of manufacturing material in a hollow fiber form to prevent complement activation and bind beta 2 microglobulin comprising the steps of forming into a tubular shape a first material having within its interior region a nucleophilic group of the structure

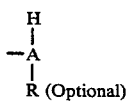

where A is an atom other than carbon;
where H is a hydrogen atom; and
where R can optionally be another H; and
simultaneously introducing into the interior region of the tubular shape a lumen fluid which includes a constituent having an activated carbonyl group which reacts with the first material to alter the nucleophilic group, the resulting structure of the nucleophilic group being

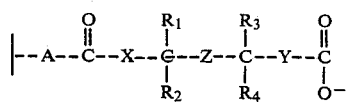

where O is a oxygen atom;
where C is a carbon atom;
where X is a sigma bond or an alkyl or alkyl derivative or an alkene or alkene derivative or an aryl compound;
where Y is a sigma bond or an alkyl or alkyl derivative or alkene or alkene derivative of an aryl compound;
where Z is a sigma bond, pi bond or an alkyl or alkyl derivative or alkene or alkene derivative or an aryl compound;
where $R_1$ is a hydrogen atom; or an alkyl or alkyl derivative; alkene or alkene derivative; or aryl compound; or a halide, or any of the following groups: COOH, $SO_3$, $SO_4$, $PO_4$, or DEAE (diethylaminioethyl) moiety; or any primary, secondary or tertiary amine, or any alkyl ether, or thio alkyl ether of the form —OR or —SR, where R is any alkyl, alkenyl or aryl chain, and S is a sulphur atom;

where $R_2$ is a hydrogen atom; or an alkyl or alkyl derivative; alkene or alkene derivative; or aryl compound; or a halide, or any of the following groups: COOH, $SO_3$, $SO_4$, $PO_4$, or DEAE (diethylaminoethyl) moiety; or any primary, secondary or tertiary amine, or any alkyl ether, or thio alkyl ether of the form —OR or —SR, where R is any alkyl, alkenyl or aryl chain, and S is a sulphur atom;

where $R_3$ is a hydrogen atom; or an alkyl or alkyl derivative; alkene or alkene derivative; or aryl compound; or a halide, or any of the following groups: COOH, $SO_3$, $SO_4$, $PO_4$, or DEAE (diethylaminoethyl) moiety; or any primary, secondary or tertiary amine, or any alkyl ether, or thio alkyl ether of the form —OR or —SR, where R is any alkyl, alkenyl or aryl chain, and S is a sulphur atom; and where $R_4$ is a hydrogen atom; or an alkyl or alkyl derivative; alkene or alkene derivative; or aryl compound; or a halide, or any of the following groups: COOH, $SO_3$, $SO_4$, $PO_4$, or DEAE (diethylaminoethyl) moiety; or any primary, secondary or tertiary amine, or any alkyl ether, or thio alkyl ether of the form —OR or —SR, where R is any alkyl, alkenyl or aryl chain, and S is a sulphur atom.

7. A method according to claim 6 wherein during said forming step, the first material is extruded through a die.

8. A method according to claim 7 wherein, during said lumen fluid introduction step, the lumen fluid includes a constituent which is immiscible with the formed material and which forms the interior bore of the hollow fiber.

9. A method according to claim 6 wherein, during said lumen fluid introduction step, the lumen fluid includes a constituent which is immiscible with the formed material and which forms the interior bore of the hollow fiber.

10. A method according to claim 6 and further including the step of removing the lumen fluid from the interior region of the tubular shape.

11. A method according to claim 1 or 6 wherein, in said step of introducing the lumen fluid, the constituent is chosen from the group consisting of dicarboxylic acid anhydrides and dicarboxylic acid halides.

12. A method according to claim 1 or 6 wherein said material is a cellulosic material.

* * * * *